United States Patent
Lin et al.

(10) Patent No.: US 10,310,131 B2
(45) Date of Patent: Jun. 4, 2019

(54) SURFACE NUCLEAR MAGNETIC RESONANCE SYSTEM EXCITED BY GEOELECTRIC FIELD FOR GROUNDWATER DETECTION AND FIELD DETECTION METHOD

(71) Applicant: JILIN UNIVERSITY, Changchun, Jilin (CN)

(72) Inventors: Tingting Lin, Jilin (CN); Yang Zhang, Jilin (CN); Ying Yang, Jilin (CN); Hongyu Wang, Jilin (CN); Kun Zhou, Jilin (CN); Ling Wan, Jilin (CN)

(73) Assignee: JILIN UNIVERSITY, Changchun, Jilin (CN)

( * ) Notice: Subject to any disclaimer, the term of this patent is extended or adjusted under 35 U.S.C. 154(b) by 77 days.

(21) Appl. No.: 15/796,438

(22) Filed: Oct. 27, 2017

(65) Prior Publication Data
US 2018/0188405 A1  Jul. 5, 2018

(30) Foreign Application Priority Data
Jan. 3, 2017 (CN) .......................... 2017 1 0000495

(51) Int. Cl.
*G01V 3/14* (2006.01)
*G01N 24/08* (2006.01)
(Continued)

(52) U.S. Cl.
CPC .............. *G01V 3/14* (2013.01); *G01N 24/081* (2013.01); *G01R 33/323* (2013.01);
(Continued)

(58) Field of Classification Search
CPC ...... G01V 3/14; G01N 24/081; G01R 33/445; G01R 33/3415; G01R 33/323; G01R 33/3614; G01R 33/3607; G01R 33/3621
See application file for complete search history.

(56) References Cited

U.S. PATENT DOCUMENTS 9,103,889 B1 *   8/2015  Fukushima .......... G01R 33/341
2008/0284426 A1 * 11/2008  Shorey ................. G01N 24/081
                                                    324/307
(Continued)

FOREIGN PATENT DOCUMENTS

CN    1936621 A    3/2007
CN  102096112 A    6/2011
CN  103033849 A    4/2013

*Primary Examiner* — G. M. A Hyder
(74) *Attorney, Agent, or Firm* — Yue (Robert) Xu; Apex Attorneys at Law, LLP

(57) ABSTRACT

Provided are a surface nuclear magnetic resonance system excited by a geoelectric field and a field working method for groundwater detection. A computer is connected to a synchronization module via a transmitter. The transmitter is connected to a first electrode and a second electrode via a transmission line. Receiving coils are symmetrically arranged on two sides of the transmission line. Each of the receivers is mounted with two receiving coils. The computer is connected to a fourth receiver via a first receiver, a second receiver, a third receiver, a sixth receiver and a fifth receiver, and the synchronization module is connected to the first receiver, the second receiver, the third receiver, the fourth receiver, the fifth receiver and the sixth receiver.

5 Claims, 3 Drawing Sheets

(51) Int. Cl.
*G01R 33/44* (2006.01)
*G01R 33/32* (2006.01)
*G01R 33/3415* (2006.01)
*G01R 33/36* (2006.01)

(52) U.S. Cl.
CPC ....... *G01R 33/3415* (2013.01); *G01R 33/445* (2013.01); *G01R 33/3607* (2013.01); *G01R 33/3614* (2013.01); *G01R 33/3621* (2013.01)

(56) References Cited

U.S. PATENT DOCUMENTS

| | | | | |
|---|---|---|---|---|
| 2012/0286779 A1* | 11/2012 | Walsh | ................ | G01R 33/44 |
| | | | | 324/309 |
| 2014/0091789 A1* | 4/2014 | Wang | ................ | G01R 33/54 |
| | | | | 324/306 |

\* cited by examiner

SURFACE NUCLEAR MAGNETIC RESONANCE SYSTEM EXCITED BY GEOELECTRIC FIELD FOR GROUNDWATER DETECTION AND FIELD DETECTION METHOD

CROSS REFERENCE TO RELATED APPLICATION

The present application claims the priority to Chinese Patent Application No. 201710000495.1, titled "SURFACE NUCLEAR MAGNETIC RESONANCE SYSTEM EXCITED BY GEOELECTRIC FIELD FOR GROUNDWATER DETECTION AND FIELD DETECTION METHOD", filed on Jan. 3, 2017 with the State Intellectual Property Office of the PRC, which is incorporated herein by reference in its entirety.

FIELD

The present disclosure relates to a geophysical exploration device and a geophysical exploration method, and in particular to a 2D/3D detection on groundwater resources performed by a surface nuclear magnetic resonance system excited by a geoelectric field, and a surface nuclear magnetic resonance system excited by a geoelectric field and a field working method, with which a large area and high efficiency detection can be achieved in a single-transmitting and multi-receiving mode.

BACKGROUND

Since the nuclear magnetic resonance groundwater detection technology is a unique geophysical method with which the groundwater can be directly detected presently, it has been widely used in groundwater resources exploration, advanced prediction of mine/tunnel disaster water source, seawater intrusion and the like. However, the existing nuclear magnetic resonance water detection instrument operates in response to excitation of a magnetic source (coils), hence it is difficult to achieve a large area measurement at a single time, and the detection efficiency is low.

In the published CN102096112, titled "Array coil-based nuclear magnetic resonance groundwater detection instrument and field detection method", multiple coils function as receiving antennas, thereby achieving a 2D/3D detection on the groundwater.

With the published CN103033849, titled "Multi-channel nuclear magnetic resonance groundwater detection instrument and field work method", not only the 2D/3D detection can be achieved, but also the anti-noise capability of the instrument is further improved with reference coils.

In the published CN1936621, titled "Nuclear magnetic resonance and transient electromagnetic combined instrument and method", two types of geophysical methods, i.e., transient electromagnetic and nuclear magnetic resonance are combined. As compared with the method based on only the nuclear magnetic resonance, a detection depth and a detection accuracy are effectively improved with the method disclosed in CN1936621. However, all of the above three methods are based on magnetic source excitation, a maximum detection area for each detection point depends on a side length of a transmission coil (the maximum side length is 150 m), and a measurement duration for each detection point is 46 minutes, hence the detection efficiency is low.

SUMMARY

An object of the present disclosure is to provide a surface nuclear magnetic resonance system excited by a geoelectric field, to overcome the above defects in the conventional technology.

Another object of the present disclosure is to provide a field detection method for a surface nuclear magnetic resonance system excited by a geoelectric field.

The objects of the present disclosure are achieved with the following technical solutions.

A surface nuclear magnetic resonance system excited by a geoelectric field, includes: a transmitter, receivers, receiving coils, a computer and a synchronization module, where the receivers include a first receiver 4, a second receiver 5, a third receiver 6, a fourth receiver 7, a fifth receiver 8 and a sixth receiver 9, the computer 1 is connected to the synchronization module 3 via the transmitter 2, the transmitter 2 is connected to an electrode A and an electrode B via a transmission line 22, the receiving coils are symmetrically arranged on two sides of the transmission line 22 connecting the electrode A and the electrode B, each of the receivers is mounted with two of the receiving coils, the computer 1 is connected to the fourth receiver 7 via the first receiver 4, the second receiver 5, the third receiver 6, the sixth receiver 9 and the fifth receiver 8, and the synchronization module 3 is connected to the first receiver 4, the fourth receiver 7, the second receiver 5, the fifth receiver 8, the third receiver 6 and the sixth receiver 9.

A spacing between the receiving coils may be 80 m, and each of the receiving coils may have a side length or a diameter of 100 m.

The transmitter 2 may include a main control circuit 23, a storage battery 24, a DC-DC charging module 25, a high power capacitor bank 26, an IGBT drive module 27, a transmitting bridge 28, a transmission line interface 29, a synchronization signal interface 30 and a communication interface 31, where the main control circuit 23 is connected to the transmission line interface 29 via the storage battery 24, the DC-DC charging module 25, the high power capacitor bank 26 and the transmitting bridge 28, the main control circuit 23 is connected to the transmitting bridge 28 via the IGBT drive module 27, and the main control circuit 23 is connected to the communication interface 31, the synchronization signal interface 30 and the DC-DC charging module 25.

Each of the receivers may include a receiving coil interface 32, a relay switching circuit 33, a bilateral diode 34, an amplifying and band-pass filtering circuit 35, a control module 36, an A/D sampling module 37, a receiving coil interface 38, a relay switching circuit 39, a bilateral diode 40, an amplifying and band-pass filtering circuit 41, a synchronization signal interface 42, a USB communication interface 43 and an RS485 interface 44, where the receiving coil interface 32 is connected to the A/D sampling module 37 via the relay switching circuit 33, the bilateral diode 34 and the amplifying and band-pass filtering circuit 35, the synchronization signal interface 42 is connected to the USB communication interface 43 and the RS485 interface 44 via the control module 36 and the A/D sampling module 37, the receiving coil interface 38 is connected to the A/D sampling module 37 via the relay switching circuit 39, the bilateral diode 40, the amplifying and band-pass filtering circuit 41, and the relay switching circuit 33 is connected to the relay switching circuit 39 via the control module 36.

A field detection method for the surface nuclear magnetic resonance system excited by a geoelectric field, includes:

step a, selecting two points A and B in a test region to fix an electrode A and an electrode B at the two points respectively, and connecting two ends of the transmission line 22 to the electrode A and the electrode B respectively, where a distance L between the point A and the point B is 1000 m;

step b, laying the receiving coils, with each of the receiving coils having a side length or a diameter of 100 m, where a first receiving coil 10, a second receiving coil 11, . . . and a twelfth receiving coil 21 are laid symmetrically on two sides of the transmission line 22, starting from the electrode A, and a spacing between the receiving coils is 80 m;

step c, connecting the transmission line 22 to the transmission line interface 29, connecting the computer 1 to a communication interface 31 of the transmitter 2, connecting the computer 1 to a USB communication interface 43 of the first receiver 4, connecting an RS485 interface 44 of the first receiver 4 to an RS485 interface 44 of the second receiver 5, connecting the RS485 interface of the second receiver 5 to an RS485 interface 44 of the third receiver 6, connecting the RS485 interface 44 of the third receiver 6 to an RS485 interface 44 of the sixth receiver 9, connecting the RS485 interface of the sixth receiver 9 to an RS485 interface 44 of the fifth receiver 8, and connecting the RS485 interface of the fifth receiver 8 to an RS485 interface 44 of the fourth receiver 7;

step d, connecting the first receiving coil 10 and the second receiving coil 11 to a receiving coil interface 32 and a receiving coil interface 38 of the first receiver 4 respectively, connecting a third receiving coil 12 and a fourth receiving coil 13 to a receiving coil interface 32 and a receiving coil interface 38 of the second receiver 5 respectively, connecting a fifth receiving coil 14 and a sixth receiving coil 15 to a receiving coil interface 32 and a receiving coil interface 38 of the third receiver 6 respectively, connecting a seventh receiving coil 16 and an eighth receiving coil 17 to a receiving coil interface 32 and a receiving coil interface 38 of the fourth receiver 7 respectively, connecting a ninth receiving coil 18 and a tenth receiving coil 19 to a receiving coil interface 32 and a receiving coil interface 38 of the fifth receiver 8 respectively, connecting an eleventh receiving coil 20 and a twelfth receiving coil 21 to a receiving coil interface 32 and a receiving coil interface 38 of the sixth receiver 9 respectively;

step e, connecting the synchronization module 3 to the transmitter 2, the first receiver 4, the second receiver 5, the third receiver 6, the fourth receiver 7, the fifth receiver 8 and the sixth receiver 9; and step f, setting a range of transmission pulse moments, the number of the transmission pulse moments, the number of times of superposition and an acquisition frequency with the computer 1, starting the surface nuclear magnetic resonance system to operate after the setting is completed, and storing detected data in a case that detection for the detection points is completed.

Beneficial effects: according to the present disclosure, a new surface magnetic resonance groundwater detection method based on geoelectric field exciting and coil receiving is provided, with which a large area and high efficiency exploration can be achieved and a problem of a low efficiency of water detection performed with the existing magnetic resonance principle can be alleviated. Since single-transmitting and multi-receiving is achieved with a synchronous circuit, it is ensured that multiple receivers operate synchronously. Communication data is transmitted by adjacent receivers, therefore it is unnecessary to use multiple parallel data transmission lines, thereby reducing a cost and a failure rate.

REFERENCE NUMERALS

Figure 1:
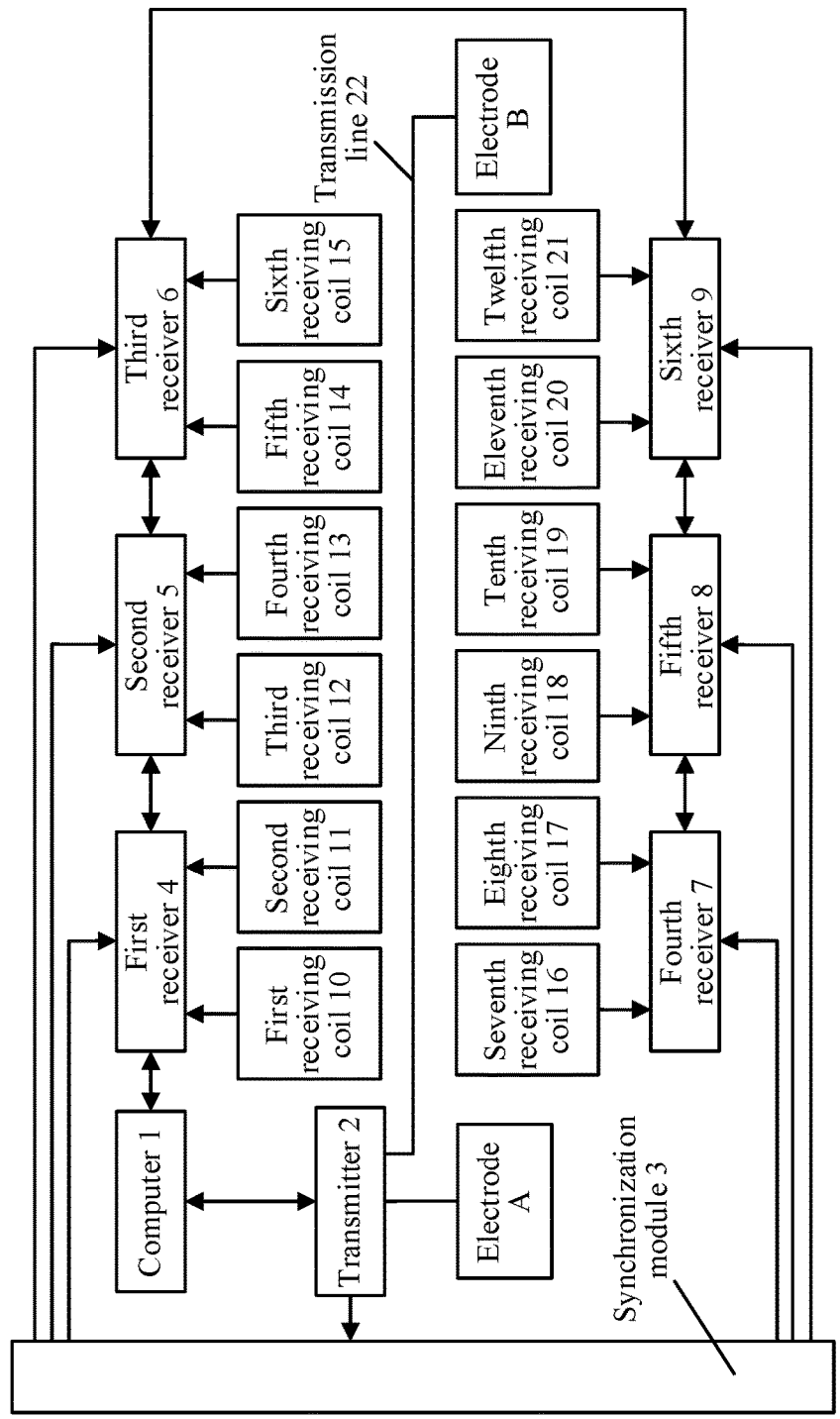
FIG. 1 is an arrangement diagram of a surface nuclear magnetic resonance system excited by a geoelectric field and a field work.

1: computer, 2: transmitter, 3: synchronization module, 4: first receiver, 5: second receiver, 6: third receiver, 7: fourth receiver, 8: fifth receiver, 9: sixth receiver, 10: first receiving coil, 11: second receiving coil, 12: third receiving coil, 13: fourth receiving coil, 14: fifth receiving coil, 15: sixth receiving coil, 16: seventh receiving coil, 17: eighth receiving coil, 18: ninth receiving coil, 19: tenth receiving coil, 20: eleventh receiving coil, 21: twelfth receiving coil, 22: transmission line, 23: main control circuit, 24: storage battery, 25: DC-DC charging module, 26: high power capacitor bank, 27: IGBT drive module, 28: transmitting bridge, 29: transmission line interface, 30: synchronization signal interface, 31: communication interface, 32: receiving coil interface, 33: relay switching circuit, 34: bilateral diode, 35: amplifying and band-pass filtering circuit a, 36: control module, 37: A/D sampling module, 38: receiving coil, 39: relay switching circuit, 40: bilateral diode, 41: amplifying and band-pass filtering circuit b, 42: synchronization signal interface, 43: USB communication interface, 44: RS485 interface.

DETAILED DESCRIPTION

The present disclosure is further described with reference to the drawings and the embodiments hereinafter.

A surface nuclear magnetic resonance system excited by a geoelectric field, includes: a transmitter 2, receivers, receiving coils, a computer 1 and a synchronization module 3, where the receivers include a first receiver 4, a second receiver 5, a third receiver 6, a fourth receiver 7, a fifth receiver 8 and a sixth receiver 9. The computer 1 is connected to the synchronization module 3 via the transmitter 2, the transmitter 2 is connected to an electrode A and an electrode B via a transmission line 22, the receiving coils are symmetrically arranged on two sides of the transmission line 22 connecting the electrode A and the electrode B, each of the receivers is mounted with two of the receiving coils, the computer 1 is connected to the fourth receiver 7 via the first receiver 4, the second receiver 5, the third receiver 6, the sixth receiver 9 and the fifth receiver 8, and the synchronization module 3 is connected to the first receiver 4, the fourth receiver 7, the second receiver 5, the fifth receiver 8, the third receiver 6 and the sixth receiver 9.

A spacing between the receiving coils is 80 m, and each of the receiving coils has a side length or a diameter of 100 m The transmitter 2 includes a main control circuit 23, a storage battery 24, a DC-DC charging module 25, a high power capacitor bank 26, an IGBT drive module 27, a transmitting bridge 28, a transmission line interface 29, a synchronization signal interface 30 and a communication interface 31, where the main control circuit 23 is connected to the transmission line interface 29 via the storage battery 24, the DC-DC charging module 25, the high power capacitor bank 26 and the transmitting bridge 28, the main control circuit 23 is connected to the transmitting bridge 28 via the IGBT drive module 27, and the main control circuit 23 is connected to the communication interface 31, the synchronization signal interface 30 and the DC-DC charging module 25.

The receiver includes a receiving coil interface 32, a relay switching circuit 33, a bilateral diode 34, an amplifying and band-pass filtering circuit 35, a control module 36, an A/D sampling module 37, a receiving coil interface 38, a relay switching circuit 39, a bilateral diode 40, an amplifying and band-pass filtering circuit 41, a synchronization signal interface 42, a USB communication interface 43 and an RS485 interface 44, where the receiving coil interface 32 is connected to the A/D sampling module 37 via the relay switching circuit 33, the bilateral diode 34 and the amplifying and band-pass filtering circuit 35, the synchronization signal interface 42 is connected to the USB communication interface 43 and the RS485 interface 44 via the control module 36 and the A/D sampling module 37, the receiving coil interface 38 is connected to the A/D sampling module 37 via the relay switching circuit 39, the bilateral diode 40, the amplifying and band-pass filtering circuit 41, and the relay switching circuit 33 is connected to the relay switching circuit 39 via the control module 36.

A field detection method for a surface nuclear magnetic resonance system excited by a geoelectric field, includes:

step a, selecting two points A and B in a test region to fix an electrode A and an electrode B at the two points respectively, and connecting two ends of the transmission line 22 to the electrode A and the electrode B respectively, where a distance L between the point A and the point B is 1000 m;

step b, laying the receiving coils, with each of the receiving coils having a side length or a diameter of 100 m, where a first receiving coil 10, a second receiving coil 11, . . . and a twelfth receiving coil 21 are laid symmetrically on two sides of the transmission line 22, starting from the electrode A, and a spacing between the adjacent receiving coils is 80 m;

step c, connecting the transmission line 22 to the transmission line interface 29, connecting the computer 1 to a communication interface 31 of the transmitter 2, connecting the computer 1 to a USB communication interface 43 of the first receiver 4, and connecting an RS485 interface 44 of the first receiver 4 to an RS485 interface 44 of the second receiver 5, connecting the RS485 interface 44 of the second receiver 5 to an RS485 interface 44 of the third receiver 6, connecting the RS485 interface 44 of the third receiver (6) to an RS485 interface 44 of the sixth receiver 9, connecting the RS485 interface 44 of the sixth receiver 9 to an RS485 interface 44 of the fifth receiver 8, and connecting the RS485 interface 44 of the fifth receiver 8 to an RS485 interface 44 of the fourth receiver 7;

step d, connecting the first receiving coil 10 and the second receiving coil 11 to a receiving coil interface 32 and a receiving coil interface 38 of the first receiver 4, connecting a third receiving coil 12 and a fourth receiving coil 13 to a receiving coil interface 32 and a receiving coil interface 38 of the second receiver 5, connecting a fifth receiving coil 14 and a sixth receiving coil 15 to a receiving coil interface 32 and a receiving coil interface 38 of the third receiver 6, connecting a seventh receiving coil 16 and an eighth receiving coil 17 to a receiving coil interface 32 and a receiving coil interface 38 of the fourth receiver 7, connecting a ninth receiving coil 18 and a tenth receiving coil 19 to a receiving coil interface 32 and a receiving coil interface 38 of the fifth receiver 8, and connecting an eleventh receiving coil 20 and a twelfth receiving coil 21 to a receiving coil interface 32 and a receiving coil interface 38 of the sixth receiver 9;

step e, connecting the synchronization module 3 to the transmitter 2, the first receiver 4, the second receiver 5, the third receiver 6, the fourth receiver 7, the fifth receiver 8 and the sixth receiver 9; and step f, setting a range of transmission pulse moments, the number of the transmission pulse moments, the number of times of superposition and an acquisition frequency with the computer 1, starting the surface nuclear magnetic resonance system to operate after the setting is completed, and storing detected data in a case that detection for the detection points is completed.

As shown in FIG. 1, in a surface nuclear magnetic resonance system excited by a geoelectric field, the computer 1 is connected to the synchronization module 3 and the transmission line 22 via the transmitter 2, the computer 1 is connected to the second receiver 5 via the first receiver 4, the second receiver 5 is connected to the sixth receiver 9 via the third receiver 6, the sixth receiver 9 is connected to the fourth receiver 7 via the fifth receiver 8, the synchronization module 3 is connected to the first receiver 4, the second receiver 5, the third receiver 6, the fourth receiver 7, the fifth receiver 8 and the sixth receiver 9, the first receiver 4 is connected to the first receiving coil 10 and the second receiving coil 11, the second receiver 5 is connected to the third receiving coil 12 and the fourth receiving coil 13, the third receiver 6 is connected to the fifth receiving coil 14 and the sixth receiving coil 15, the fourth receiver 7 is connected to the seventh receiving coil 16 and the eighth receiving coil 17, the fifth receiver 8 is connected to the ninth receiving coil 18 and the tenth receiving coil 19, and the sixth receiver 9 is connected to the eleventh receiving coil 20 and the twelfth receiving coil 21.

Figure 2:
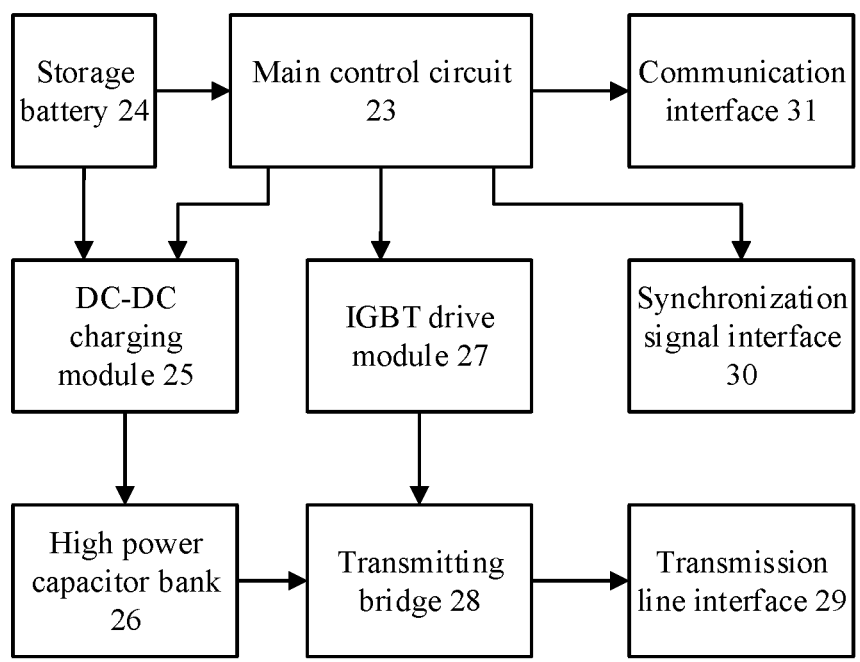
FIG. 2 is a structural block diagram of a transmitter 2 shown in FIG. 1.

As shown in FIG. 2, the transmitter 2 includes the main control circuit 23, the storage battery 24, the DC-DC charging module 25, the high power capacitor bank 26, the IGBT drive module 27, the transmitting bridge 28, the transmission line interface 29, the synchronization signal interface 30 and the communication interface 31. The main control circuit 23 is connected to the DC-DC charging module 25 via the storage battery 24. The main control circuit 23 is connected to the transmitting bridge 28 via the IGBT drive module 27. The main control circuit 23 is connected to the communication interface 31 and the synchronization signal interface 30. The DC-DC charging module 25 is connected to the transmitting bridge via the high power capacitor bank 26. The transmitting bridge 28 is connected to the transmission line interface 29.

Figure 3:
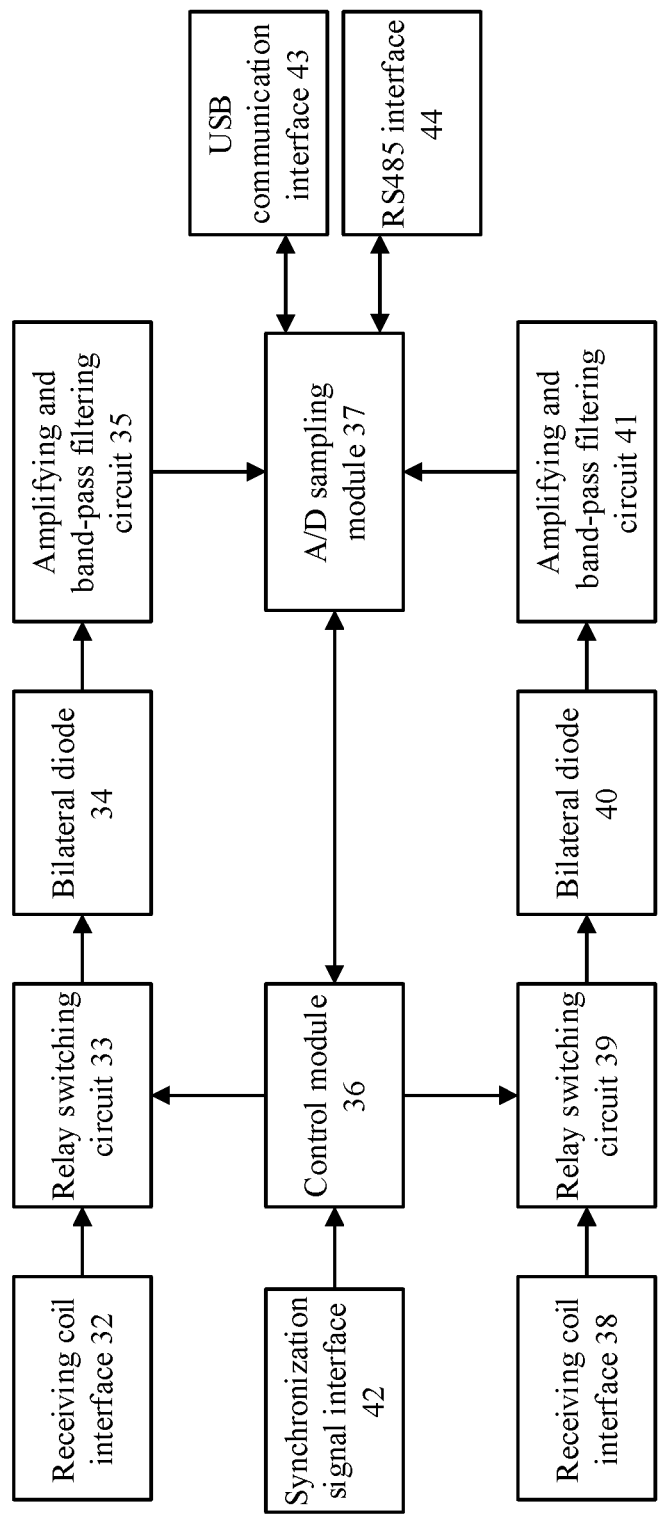
FIG. 3 is a structural block diagram of a receiver shown in FIG. 1.

As shown in FIG. 3, the first receiver 4, the second receiver 5, the third receiver 6, the fourth receiver 7, the fifth receiver 8 and the sixth receiver 9 have the same structure which is described as follows. Each of the receivers includes the receiving coil interface 32, the relay switching circuit 33, the bilateral diode 34, the amplifying and band-pass filtering circuit 35, the control module 36, the A/D sampling module 37, the receiving coil interface 38, the relay switching circuit 39, the bilateral diode 40, the amplifying and band-pass filtering circuit 41, the synchronization signal interface 42, the USB communication interface 43 and the RS485 interface 44. The receiving coil interface 32 is connected to the bilateral diode 34 via the relay switching circuit 33. The bilateral diode 34 is connected to the A/D sampling module 37 via the amplifying and band-pass filtering circuit 35. The synchronization signal interface 42 is connected to the A/D sampling module 37 via the control module 36. The A/D sampling module 37 is connected to both the USB communication interface 43 and the RS485 interface 44. The receiving coil interface 38 is connected to the bilateral diode 40 via the relay switching circuit 39. The bilateral diode 40 is connected to the A/D sampling module 37 via the amplifying and band-pass filtering circuit 41. The control module 36 is connected to both the relay switching circuit 33 and the relay switching circuit 39.

A field detection method for a surface nuclear magnetic resonance system excited by a geoelectric field, includes:

step a, selecting two points A and B in a test region to fix electrodes A and B at the two points respectively, and connecting two ends of the transmission line 22 to the electrode A and the electrode B respectively, where a distance L between the point A and the point B is 1000 m;

step b, laying receiving coils, with each of the receiving coils having a side length or a diameter of 100 m, where a first receiving coil 10, a second receiving coil 11, . . . and a twelfth receiving coil 21 are symmetrically laid on two sides of the transmission line 22, starting from the electrode A, and a spacing between the adjacent receiving coils is 80 m;

step c, connecting the transmission line 22 to the transmission line interface 29, connecting the computer 1 to the communication interface 31 of the transmitter 2, connecting the computer 1 to the USB communication interface 43 of the first receiver 4, connecting the RS485 interface 44 of the first receiver 4 to the RS485 interface 44 of the second receiver 5, connecting the RS485 interface 44 of the second receiver 5 to the RS485 interface 44 of the third receiver 6, connecting the RS485 interface 44 of the third receiver 6 to the RS485 interface 44 of the sixth receiver 9, connecting the RS485 interface 44 of the sixth receiver 9 to the RS485 interface 44 of the fifth receiver 8, and connecting the RS485 interface 44 of the fifth receiver 8 to the RS485 interface 44 of the fourth receiver 7;

step d, connecting the first receiving coil 10 and the second receiving coil 11 respectively to the receiving coil interface 32 and the receiving coil interface 38 of the first receiver 4, connecting the third receiving coil 12 and the fourth receiving coil 13 respectively to the receiving coil interface 32 and the receiving coil interface 38 of the second receiver 5, connecting the fifth receiving coil 14 and the sixth receiving coil 15 respectively to the receiving coil interface 32 and the receiving coil interface 38 of the third receiver 6, connecting the seventh receiving coil 16 and the eighth receiving coil 17 respectively to the receiving coil interface 32 and the receiving coil interface 38 of the fourth receiver 7, connecting the ninth receiving coil 18 and the tenth receiving coil 19 respectively to the receiving coil interface 32 and the receiving coil interface 38 of the fifth receiver 8, and connecting the eleventh receiving coil 20 and the twelfth receiving coil 21 respectively to the receiving coil interface 32 and the receiving coil interface 38 of the sixth receiver 9;

step e, connecting the synchronization module 3 to the transmitter 2, the first receiver 4, the second receiver 5, the third receiver 6, the fourth receiver 7, the fifth receiver 8 and the sixth receiver 9; and step f, setting a range of transmission pulse moments, the number of transmission pulse moments, the number of times of superposition and an acquisition frequency with the computer 1, starting the surface nuclear magnetic resonance system to operate after the setting is completed, and storing detected data in a case that detection for the detection points is completed.

Embodiment

In the Shaoguo town of Changchun, the surface nuclear magnetic resonance system excited by a geoelectric field and the field detection method for the system according to the present disclosure are applied practically in the field.

The implementation includes steps a to f in the following.

In step a, two points A and B are selected in a test region to fix electrodes A and B respectively at the two points, and two ends of the transmission line 22 are connected respectively to the electrode A and the electrode B, where a distance L between the point A and the point B is 1000 m.

In step b, receiving coils are laid, with each of the receiving coils having a side length or a diameter of 100 m. The first receiving coil 10, the second receiving coil 11, . . . , and the twelfth receiving coil 21 are laid symmetrically on two sides of the transmission line 22, starting from the electrode A, and a spacing between the receiving coils is 80 m.

In step c, the transmission line 22 is connected to the transmission line interface 29, the computer 1 is connected to the communication interface 31 of the transmitter 2, the computer 1 is connected to the USB communication interface 43 of the first receiver 4, the RS485 interface 44 of the first receiver 4 is connected to the RS485 interface 44 of the second receiver 5, the RS485 interface 44 of the second receiver 5 is connected to the RS485 interface 44 of the third receiver 6, the RS485 interface 44 of the third receiver 6 is connected to the RS485 interface 44 of the sixth receiver 9, the RS485 interface 44 of the sixth receiver 9 is connected to the RS485 interface 44 of the fifth receiver 8, and the RS485 interface 44 of the fifth receiver 8 is connected to the RS485 interface 44 of the fourth receiver 7.

In step d, the first receiving coil 10 and the second receiving coil 11 are connected respectively to the receiving coil interface 32 and the receiving coil interface 38 of the first receiver 4, the third receiving coil 12 and the fourth receiving coil 13 are connected respectively to the receiving coil interface 32 and the receiving coil interface 38 of the second receiver 5, the fifth receiving coil 14 and the sixth receiving coil 15 are connected respectively to the receiving coil interface 32 and the receiving coil interface 38 of the third receiver 6, the seventh receiving coil 16 and the eighth receiving coil 17 are connected respectively to the receiving coil interface 32 and the receiving coil interface 38 of the fourth receiver 7, the ninth receiving coil 18 and the tenth receiving coil 19 are connected respectively to the receiving coil interface 32 and the receiving coil interface 38 of the fifth receiver 8, and the eleventh receiving coil 20 and the twelfth receiving coil 21 are connected respectively to the receiving coil interface 32 and the receiving coil interface 38 of the sixth receiver 9.

In step e, the synchronization module 3 is connected to the transmitter 2, the first receiver 4, the second receiver 5, the third receiver 6, the fourth receiver 7, the fifth receiver 8 and the sixth receiver 9.

In step f, the range of transmission pulse moments is set as 200 A·ms to 10000 A·ms, the number of transmission pulse moments is set as 16, the number of times of superposition is set as 32 and the acquisition frequency is set as 25 kHz, with the computer 1. In the case that the setting is completed, the water detection system is started to operate, and detected data is stored until a test at the detection points is completed.

In a case that the test ends, signal processing is performed on the data acquired by each of the receivers. It can be seen from the spectrum that, there is a signal at a frequency point of 2330 Hz (the Larmor frequency of a detection point), and it can be seen from the time domain that there is a Sinusoidal signal attenuating by an e exponent, i.e., a magnetic resonance signal. In addition, signals acquired by the second receiver and the fifth receiver have larger signal amplitudes while signals acquired by the first, third, fourth and sixth receivers have smaller signal amplitudes, which conforms to theoretical analysis and proves the effectiveness of the detected data.

The invention claimed is:

1. A surface nuclear magnetic resonance system excited by a geoelectric field, comprising:
   a transmitter;
   receivers;
   receiving coils;
   a computer; and
   a synchronization module, wherein
   the receivers comprise a first receiver, a second receiver, a third receiver, a fourth receiver, a fifth receiver and a sixth receiver,
   the computer is connected to the synchronization module via the transmitter,
   the transmitter is connected to a first electrode and a second electrode via a transmission line,
   the receiving coils are symmetrically arranged on two sides of the transmission line connecting the first electrode and the second electrode, each of the receivers is mounted with two of the receiving coils,
   the computer is connected to the fourth receiver via the first receiver, the second receiver, the third receiver, the sixth receiver and the fifth receiver, and
   the synchronization module is connected to the first receiver, the fourth receiver, the second receiver, the fifth receiver, the third receiver and the sixth receiver.

2. The surface nuclear magnetic resonance system excited by the geoelectric field according to claim 1, wherein a spacing between the receiving coils is 80 m, and each of the receiving coils has a side length or a diameter of 100 m.

3. The surface nuclear magnetic resonance system excited by the geoelectric field according to claim 1, wherein the transmitter comprises:
   a main control circuit;
   a storage battery;
   a DC-DC charging module;
   a high power capacitor bank;
   an IGBT drive module;
   a transmitting bridge;
   a transmission line interface;
   a synchronization signal interface; and
   a communication interface; and wherein
   the main control circuit is connected to the transmission line interface via the storage battery, the DC-DC charging module, the high power capacitor bank and the transmitting bridge,
   the main control circuit is connected to the transmitting bridge via the IGBT drive module, and
   the main control circuit is connected to the communication interface, the synchronization signal interface and the DC-DC charging module.

4. The surface nuclear magnetic resonance system excited by the geoelectric field according to claim 1, wherein each of the receivers comprises:
   a first receiving coil interface;
   a first relay switching circuit;
   a first bilateral diode;
   a first amplifying and band-pass filtering circuit;
   a control module;
   an A/D sampling module;
   a second receiving coil interface;
   a second relay switching circuit;
   a second bilateral diode;
   a second amplifying and band-pass filtering circuit;
   a synchronization signal interface;
   a USB communication interface; and
   an RS485 interface; and wherein
   the first receiving coil interface is connected to the A/D sampling module via the first relay switching circuit, the first bilateral diode and the first amplifying and band-pass filtering circuit,
   the synchronization signal interface is connected to the USB communication interface and the RS485 interface via the control module and the A/D sampling module,
   the second receiving coil interface is connected to the A/D sampling module via the second relay switching circuit, the second bilateral diode, the second amplifying and band-pass filtering circuit, and
   the first relay switching circuit is connected to the second relay switching circuit via the control module.

5. A field detection method for the surface nuclear magnetic resonance system excited by the geoelectric field according to claim 1, comprising:
   step a, selecting two points in a test region to fix a first electrode and a second electrode at the two points respectively, and connecting two ends of the transmission line to the first electrode and the second electrode respectively, wherein a distance L between the two points is 1000 m;
   step b, laying the receiving coils, with each of the receiving coils having a side length or a diameter of 100 m, wherein a first receiving coil, a second receiving coil, . . . and a twelfth receiving coil are laid symmetrically on two sides of the transmission line, starting from the first electrode, and a spacing between the receiving coils is 80 m;
   step c,
      connecting the transmission line to the transmission line interface,
      connecting the computer to a communication interface of the transmitter and a USB communication interface of the first receiver,
      connecting an RS485 interface of the first receiver to an RS485 interface of the second receiver,
      connecting the RS485 interface of the second receiver to an RS485 interface of the third receiver,
      connecting the RS485 interface of the third receiver to an RS485 interface of the sixth receiver,
      connecting the RS485 interface of the sixth receiver to an RS485 interface of the fifth receiver, and
      connecting the RS485 interface of the fifth receiver to an RS485 interface of the fourth receiver;
   step d,
      connecting the first receiving coil and the second receiving coil to a first receiving coil interface and a second receiving coil interface of the first receiver respectively,
      connecting a third receiving coil and a fourth receiving coil to a first receiving coil interface and a second receiving coil interface of the second receiver respectively,
      connecting a fifth receiving coil and a sixth receiving coil to a first receiving coil interface and a second receiving coil interface of the third receiver respectively, connecting a seventh receiving coil and an eighth receiving coil to a first receiving coil interface and a second receiving coil interface of the fourth receiver respectively, connecting a ninth receiving coil and a tenth receiving coil to a first receiving coil interface and a second receiving coil interface of the fifth receiver respectively, connecting an eleventh receiving coil and a twelfth receiving coil to a first receiving coil interface and a second receiving coil interface of the sixth receiver respectively; and step e, setting a range of transmission pulse moments, the number of the transmission pulse moments, the number of times of superposition and an acquisition frequency with the computer, starting the surface nuclear magnetic resonance system to operate after the setting is completed, and storing detected data in a case that detection for the detection points is completed.

* * * * *